US008070041B2

(12) United States Patent
Rauguth et al.

(10) Patent No.: US 8,070,041 B2
(45) Date of Patent: Dec. 6, 2011

(54) DIRECT APPLICATION OF PRESSURE FOR BONDING POROUS COATINGS TO SUBSTRATE MATERIALS USED IN ORTHOPAEDIC IMPLANTS

(75) Inventors: Brad L. Rauguth, North Webster, IN (US); William G. Hutchison, Warsaw, IN (US); Clarence M. Panchison, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 12/704,930

(22) Filed: Feb. 12, 2010

(65) Prior Publication Data

US 2010/0143576 A1 Jun. 10, 2010

Related U.S. Application Data

(62) Division of application No. 11/681,268, filed on Mar. 2, 2007, now Pat. No. 7,686,203.

(60) Provisional application No. 60/889,043, filed on Feb. 9, 2007.

(51) Int. Cl.
  *B23K 20/02* (2006.01)
(52) U.S. Cl. .................. 228/102; 228/193; 228/234.1
(58) Field of Classification Search .................. None
  See application file for complete search history.

(56) References Cited

U.S. PATENT DOCUMENTS

| | | | |
|---|---|---|---|
| 3,727,299 A * | 4/1973 | Hoffmann et al. ............ 228/121 |
| 4,089,456 A | 5/1978 | Toppen et al. | |
| 4,444,352 A | 4/1984 | Glascock et al. | |
| 4,570,271 A | 2/1986 | Sump | |
| 4,603,808 A * | 8/1986 | Stacher ......................... 228/265 |
| 4,635,461 A | 1/1987 | Raymond | |
| 4,636,219 A * | 1/1987 | Pratt et al. .................... 623/23.3 |
| 4,650,109 A * | 3/1987 | Crivella et al. ............... 228/194 |
| 4,660,755 A * | 4/1987 | Farling et al. ................. 228/178 |
| 4,800,639 A * | 1/1989 | Frey et al. .................... 29/421.1 |
| 4,813,965 A * | 3/1989 | Roberts ......................... 623/3.16 |
| 4,854,496 A | 8/1989 | Bugle | |
| 5,027,998 A | 7/1991 | Bugle | |
| 5,044,546 A * | 9/1991 | De Clerck .................... 228/194 |
| 5,139,528 A * | 8/1992 | Koch et al. ................... 29/469.5 |
| 5,201,766 A | 4/1993 | Georgette | |
| 5,255,838 A * | 10/1993 | Gladdish et al. ............. 228/135 |
| 5,323,954 A * | 6/1994 | Shetty et al. .................. 228/187 |

(Continued)

FOREIGN PATENT DOCUMENTS

| | | |
|---|---|---|
| EP | 1433443 A1 | 6/2004 |
| SU | 193285 A | 4/1977 |

OTHER PUBLICATIONS

The European search report published as EP1955675A1 on Aug. 13, 2008 in the related European application No. EP08250430.9.

(Continued)

*Primary Examiner* — Kiley Stoner
(74) *Attorney, Agent, or Firm* — Baker & Daniels LLP

(57) ABSTRACT

A method for constantly controlling a direct application of pressure for bonding porous coatings to substrate materials used in orthopaedic implants. The direct pressure is applied to an interface between the porous coating and the substrate material via a pressure application mechanism unaffected by heat and air pressure conditions of the bonding process. The pressure application mechanism maintains a pressure on the implant which is constantly controlled throughout the bonding process.

22 Claims, 2 Drawing Sheets

U.S. PATENT DOCUMENTS

| | | | |
|---|---|---|---|
| 5,466,530 | A | 11/1995 | England |
| 5,484,098 | A | 1/1996 | Anttila et al. |
| 5,504,300 | A * | 4/1996 | Devanathan et al. .... 219/121.64 |
| 5,648,176 | A * | 7/1997 | Nakagawa et al. ........... 428/593 |
| 5,672,284 | A * | 9/1997 | Devanathan et al. .... 219/121.64 |
| 5,755,806 | A * | 5/1998 | Stalcup et al. ................ 128/898 |
| 6,945,448 | B2 | 9/2005 | Medlin |
| 2004/0144835 | A1 | 7/2004 | Clifford |
| 2005/0112397 | A1 | 5/2005 | Rolfe et al. |
| 2005/0184134 | A1 | 8/2005 | Charlesbois |
| 2005/0242162 | A1* | 11/2005 | Medlin et al. ................. 228/194 |
| 2007/0191929 | A1* | 8/2007 | Osborne et al. .............. 623/1.16 |

OTHER PUBLICATIONS

The Response filed Feb. 4, 2009 to the European search report dated Jun. 9, 2009 in the related European application No. EP08250430.9.

The Office Action mailed Apr. 10, 2009 in related U.S. Appl. No. 11/681,268.

The Amendment filed Aug. 3, 2009 in response to the Apr. 10, 2009 Office Action in related U.S. Appl. No. 11/681,268.

The Final Office Action mailed Sep. 21, 2009 in related U.S. Appl. No. 11/681,268.

The Amendment After Final filed Nov. 10, 2009 in response to the Sep. 21, 2009 Final Office Action in related U.S. Appl. No. 11/681,268.

* cited by examiner

DIRECT APPLICATION OF PRESSURE FOR BONDING POROUS COATINGS TO SUBSTRATE MATERIALS USED IN ORTHOPAEDIC IMPLANTS

CROSS REFERENCE TO RELATED APPLICATIONS

This application is a division of U.S. patent application Ser. No. 11/681,268, filed Mar. 2, 2007 now U.S. Pat. No. 7,686,203, which claims the benefit under 35 U.S.C. §119(e) of U.S. Provisional Patent Application Ser. No. 60/889,043, filed Feb. 9, 2007, both entitled DIRECT APPLICATION OF PRESSURE FOR BONDING POROUS COATINGS TO SUBSTRATE MATERIALS USED IN ORTHOPAEDIC IMPLANTS, the disclosures of which are hereby expressly incorporated herein by reference.

BACKGROUND

1. Field of the Invention

The present invention relates to orthopaedic implants, and, more particularly, to orthopaedic implants having a porous coating attached to the surface. The present invention also relates to methods for bonding coatings to substrate materials. More particularly, the present invention relates to methods for controlling a direct application of pressure for bonding porous coatings to substrate materials used in orthopaedic implants.

2. Description of the Related Art

Orthopaedic implants commonly include a metal substrate and a porous structure of a desired thickness on a bone contacting surface of the implant to promote bone growth therethrough and to enhance attachment of the implant to adjacent bone tissue. Various methods have been developed for manufacturing an orthopaedic implant having a porous surface, including plasma spraying, sintering, and diffusion bonding.

Orthopaedic implants, such as hip, knee, elbow, shoulder, and spine, for example, may include one or more porous surfaces to allow bone ingrowth for fixation. Typically, the porous materials are prepared and attached to a substrate material. The porous coatings may be pre-sintered or diffusion bonded prior to attachment to a substrate material. The porous coatings are then attached to the substrate to form a metallurgical bond with the substrate with a variety of heat treatment processes.

Contact between the substrate and the porous coating may be maintained to achieve a metallurgical bond during the entire heat treatment process. This can be achieved with fixtures formed of high temperature materials that are inert and do not react with the implant. In addition, the temperatures required to achieve a metallurgical bond are substantially high and may require the use of a vacuum furnace so that the surface of the parts are not chemically altered. The heat treatment processes utilized to achieve a metallurgical bond between the substrate and the porous coating can be approximately 14 hours with multiple iterations required. The total cycle time can be in excess of 28 hours.

SUMMARY

The present invention provides a method for constantly controlling a direct application of pressure for bonding porous coatings to substrate materials used in orthopaedic implants. The direct pressure is applied to an interface between the porous coating and the substrate material via a pressure application mechanism unaffected by heat and air pressure conditions of the bonding process. The pressure application mechanism maintains a pressure on the implant which is constantly controlled throughout the bonding process.

Moreover, the present invention provides a method of greatly decreasing the required time to achieve a metallurgical bond. Implants can be processed with conventional heat treatment practices while providing an opportunity to continuously control and monitor applied pressure by an external means. By constantly and consistently controlling applied pressure, the cycle time required to form a metallurgical bond between the substrate, inter-layers, and porous coating surfaces can be reduced.

In one form thereof, the present invention provides a method for bonding a coating to a substrate to form an orthopaedic implant, including the steps of providing an implant including at least a substrate and a coating; applying pressure to the implant; constantly controlling said applied pressure; and bonding the implant during said applying step.

In another form thereof, the present invention provides an apparatus for bonding a coating to a substrate to form an orthopaedic implant, including pressure means for applying pressure to the implant; control means for controlling the applied pressure; and bonding means for bonding the substrate and the coating while said control means maintains the applied pressure.

In yet another form thereof, the present invention provides a system for manufacturing an orthopaedic component, including an implant including at least a first layer and a second layer; a furnace, said implant disposed in said furnace; a pressure applicator, said pressure applicator associated with said furnace; and a controller, said controller associated with said pressure applicator.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein.

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
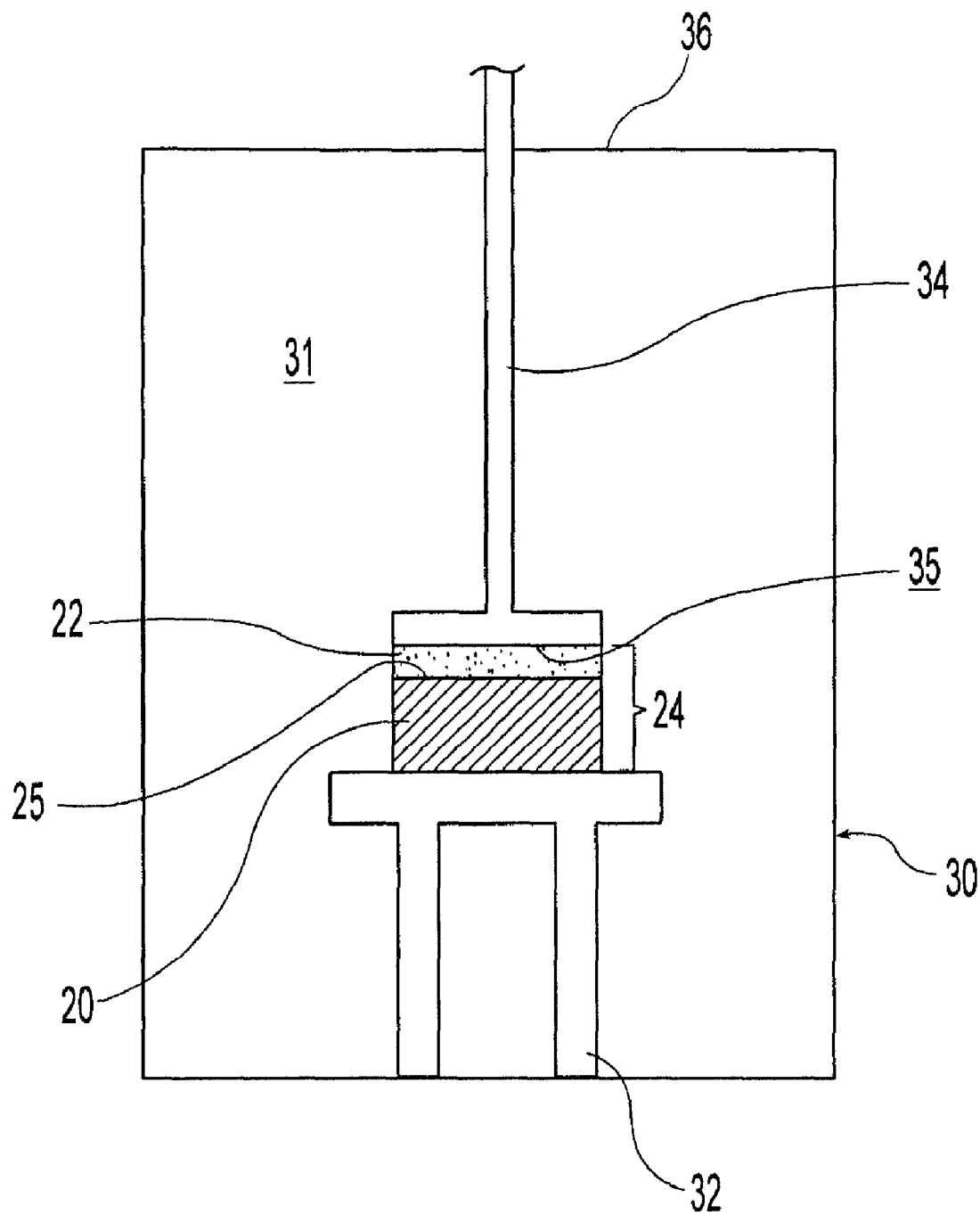
FIG. 1 is a plan view of an apparatus useable with a method according to an embodiment of the present disclosure.
Figure 2:
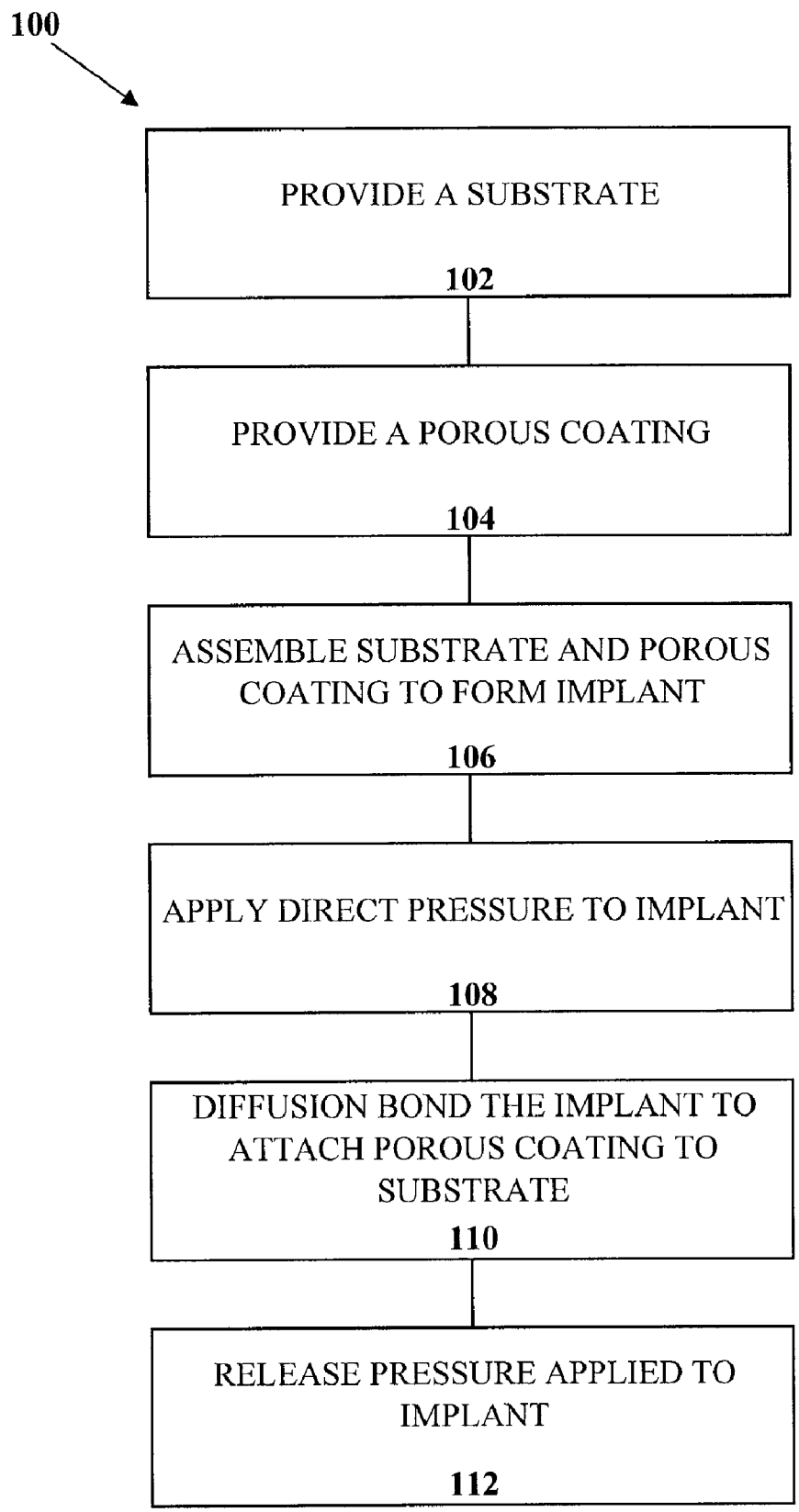
FIG. 2 is a schematic diagram of a method according to an embodiment of the present disclosure.

Referring now to FIG. 2, method 100 according to one embodiment of the present disclosure includes several steps represented by Blocks 102, 104, 106, 108, 110, and 112. Block 102 represents the step of providing substrate 20 (FIG. 1). In an exemplary embodiment, substrate 20 may be a metal substrate, such as a titanium based or cobalt based alloy, for example, which are often used in orthopaedic implants. Examples of titanium based alloys include Ti-6Al-4V alloy or Ti-6Al-7Nb alloy having a rating of ASTM F-136 or F-1295, respectively. Examples of cobalt based alloys include cast cobalt chromium molybdenum (CoCrMo) alloys or wrought CoCrMo alloys having an ASTM designation of F-75 or F-1537, respectively. In one embodiment, substrate 20 (FIG.

1) is shaped as a component of an orthopaedic implant, such as an acetabular cup or a femoral component for a prosthetic knee, for example.

Referring still to FIG. 2, Block 104 represents the step of providing porous coating 22 (FIG. 1), such as a porous metal layer, thin film, powder, beads, and/or foils, for example. In one embodiment, porous coating 22 includes a porous tantalum structure. Porous coating 22 may also be formed with Trabecular Metal™, commercially pure titanium fiber metal, or CoCrMo fiber metal. In an exemplary embodiment, porous coating 22 is provided in a shape suitable for use on a bone-contacting surface of an orthopaedic implant, such as an acetabular cup shell or a femoral component for a prosthetic knee, for example.

Block 106 represents the step of assembling porous coating 22 and substrate 20 at interface 25 to form implant 24 (FIG. 1). The process continues with Block 108 and Block 110 representing concurrent steps of directly applying pressure to implant 24 while simultaneously diffusion bonding implant 24, i.e., while simultaneously heating implant 24.

In order to provide a strong metallurgical bond between substrate 20 and porous coating 22 via sintering or diffusion bonding, there must be sufficient surface contact between substrate 20 and porous coating 22 at interface 25. On a microscopic level, neither the surface of substrate 20 nor the surface of porous coating 22 is perfectly contoured. Thus, application of pressure is necessary by some mechanism to ensure adequate contact between porous coating 22 and substrate 20 that achieves a bond interface 25.

In Block 108, pressure is applied to implant 24, i.e., to interface 25 between porous coating 22 and substrate 20. Advantageously, the pressure is controlled by a system which is immune to the temperature and air pressure conditions inside vacuum chamber 31; therefore, the system is able to constantly control a constant or varying pressure applied to implant 24 during the entire bonding process.

Referring to FIG. 1, implant 24 is first placed on support structure 32 in vacuum chamber 31 of vacuum furnace 30. Vacuum furnace 30 provides a vacuum or controlled atmosphere for diffusion bonding. Press or ram 34 extends through wall 36 of vacuum furnace 30 and abuts implant 24 such that physical surface contact may occur between impact surface 35 of press 34 and porous coating 22. Alternatively, implant 24 may be positioned such that impact surface 35 directly contacts the surface of substrate 20 or both substrate 20 and porous coating 22. In another embodiment, an auxiliary fixture (not shown) may be utilized between impact surface 35 and implant 24. The auxiliary fixture may include a shape configured to match implant 24, such as a hemispherical shape when implant 24 is an acetabular shell, for example. The auxiliary fixture facilitates accommodating any shape of implant 24 while maintaining use of press 34.

Support structure 32 provides support for implant 24 during application of pressure and diffusion bonding. Support structure 32 may be advantageously arranged to provide an equal and opposite force compared to press 34 such that implant 24 does not move during application of pressure from press 34, thereby enhancing the efficiency of the pressure application. Thus, press 34 provides the capability to apply direct pressure to interface 25 of implant 24 during a diffusion bonding process, as described below. The pressure is advantageously constantly controlled throughout the diffusion bonding process. In an exemplary embodiment, applied pressure to implant 24 is constantly controlled by ramping up the load exerted by impact surface 35 of press 34 on implant 24 from 10 lbf to 5000 lbf throughout the bonding process. In one embodiment, once vacuum chamber 31 of furnace 30 reaches a desired temperature, the pressure applied to implant 24 is controlled and maintained at a constant level throughout the entire bonding or heating process. Alternatively, the pressure applied to implant 24 is controlled to be variable, i.e., the pressure may be increased and/or decreased during the bonding process. Pressure may also be applied in multiple orientations, e.g., from a single, individual orientation and/or from multiple orientations.

Impact surface 35 of press 34 may be formed of an inert material such that surface 35 does not bond or interact with either substrate 20, porous coating 22, or an auxiliary fixture during the diffusion bonding process. In one embodiment, impact surface 35 and/or the auxiliary fixture may be formed of high temperature metal components and/or graphite components, high temperature ceramic, graphite, and metal components, for example. Vacuum furnaces with acceptable atmospheric control may be used to maintain product integrity.

Referring again to FIG. 2, the diffusion bonding process is represented by Block 110 which occurs simultaneous with the pressure application step represented by Block 108. Diffusion bonding is defined as a solid-state process for joining materials by using only heat and pressure to achieve atomic bonding. An external system immune to the conditions within vacuum furnace 30 may control the pressure exerted on implant 24 throughout the bonding process. The diffusion bonding may be run at full vacuum, partial pressure, or positive pressure inside vacuum furnace 30. Advantageously, by controlling the pressure directly applied to interface 25 of implant 24 throughout the bonding process, sufficient bonding of porous coating 22 and substrate 20 may be achieved with shorter manufacturing cycle times and lower bonding temperatures as compared to conventional processes. Furthermore, the number of manufacturing cycles may be decreased as compared to conventional processes. The resultant increased control of the microstructure of substrate 20 and porous coating 22 at interface 25 may result in enhanced control of mechanical properties and fatigue strength of implant 24 as compared to conventional implants.

After diffusion bonding is complete, the pressure applied directly to implant 24 may be released in the step represented by Block 112. Implant 24 may subsequently be cooled under vacuum, partial pressure inert gas, or gas fan cooled/quenched at positive pressure.

Although described throughout as having substrate 20 and porous coating 22, implant 24 may include more than two layers, such as having intermediate layer(s) between substrate 20 and porous coating 22.

Test samples and prosthetic implants have been produced with this process to acceptable performance requirements. All samples were analyzed for microstructure (substrate, coating, and bonded interface), composition, and coating adherence strength. Samples were processed at typical temperatures required for diffusion bonding with potential benefits of reduced cycles and shorter cycle times.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method for bonding a coating to a substrate to form an orthopaedic implant, the method comprising the steps of:

providing an implant including at least a substrate and a coating;

placing the implant inside a furnace;

applying pressure to the implant with a press located inside the furnace;

constantly controlling the applied pressure, the controlling step being immune to the temperature inside the furnace; and bonding the implant during the applying step.

2. The method of claim 1, wherein the bonding step comprises the step of diffusion bonding.

3. The method of claim 1, further comprising the step of releasing the applied pressure subsequent to the bonding step.

4. The method of claim 1, wherein the controlling step comprises constantly controlling the applied pressure at a constant pressure.

5. The method of claim 1, wherein the controlling step comprises constantly controlling the applied pressure at a variable pressure.

6. The method of claim 1, wherein the coating comprises a porous coating.

7. The method of claim 1, wherein the applying pressure step comprises applying direct pressure to the implant with the press.

8. A method for bonding a coating to a substrate to form an orthopaedic implant, the method comprising the steps of:

providing an implant including at least a substrate and a coating;

placing the implant inside a furnace;

supplying heat to the implant from the furnace; and applying pressure to the implant with a press located inside the furnace to bond the coating to the substrate, the applied pressure being independent of the supplied heat.

9. The method of claim 8, wherein the supplying heat step is performed under a vacuum.

10. The method of claim 8, wherein the applying pressure step comprises applying direct pressure to the implant with the press.

11. The method of claim 10, wherein the press is immune to the supplied heat.

12. The method of claim 8, wherein the applying pressure step comprises applying direct pressure to the implant in more than one orientation.

13. The method of claim 8, wherein the applying pressure step comprises applying a constant pressure to the implant.

14. The method of claim 8, wherein the applying pressure step comprises applying a variable pressure to the implant.

15. The method of claim 8, wherein the applied pressure increases during the supplying heat step.

16. The method of claim 8, wherein the applying pressure step begins after the supplying heat step, the implant reaching a desired elevated temperature before the applying pressure step begins.

17. A method for bonding a coating to a substrate to form an orthopaedic implant, the method comprising the steps of:

providing an implant including at least a substrate and a coating;

placing the implant inside a furnace;

heating the implant inside the furnace; and applying pressure to the implant with a press located inside the furnace to bond the coating to the substrate, the applied pressure being controlled by a controller that operates independently of the furnace.

18. The method of claim 17, further comprising the step of evacuating the furnace, wherein the heating step is performed under a vacuum.

19. The method of claim 17, wherein the controller is immune to conditions inside the furnace.

20. The method of claim 7, wherein the press is hemispherical in shape.

21. The method of claim 1, further comprising the step of cooling the implant under one of a vacuum, an inert gas, and a positive pressure using a gas fan.

22. The method of claim 17, wherein the controller is external to the furnace.

* * * * *